(12) United States Patent
Foster et al.

(10) Patent No.: US 8,271,097 B2
(45) Date of Patent: Sep. 18, 2012

(54) MRI SAFE, MULTIPOLAR ACTIVE FIXATION STIMULATION LEAD WITH CO-RADIAL CONSTRUCTION

(75) Inventors: Arthur J. Foster, Centerville, MN (US); James G. Bentsen, North St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 175 days.

(21) Appl. No.: 12/907,379

(22) Filed: Oct. 19, 2010

(65) Prior Publication Data

US 2011/0160817 A1 Jun. 30, 2011

Related U.S. Application Data

(60) Provisional application No. 61/291,553, filed on Dec. 31, 2009.

(51) Int. Cl.
*A61N 1/05* (2006.01)
(52) U.S. Cl. ............ 607/116; 607/119; 607/122
(58) Field of Classification Search .......... 607/63, 607/116, 119, 122, 126–128
See application file for complete search history.

(56) References Cited

U.S. PATENT DOCUMENTS

| | | |
|---|---|---|
| 2005/0267557 A1 | 12/2005 | Flynn et al. |
| 2009/0157156 A1 | 6/2009 | Foster |
| 2009/0198314 A1 | 8/2009 | Foster et al. |

FOREIGN PATENT DOCUMENTS

EP 1426079 6/2004

OTHER PUBLICATIONS

International Search Report and Written Opinion issued in PCT/US2010/053179, mailed May 24, 2011, 11 pages.

*Primary Examiner* — Carl H Layno
*Assistant Examiner* — Yun Haeng Lee
(74) *Attorney, Agent, or Firm* — Faegre Baker Daniels LLP

(57) ABSTRACT

Various embodiments relating to MRI safe, multi-polar active fixation stimulation leads with co-radial construction are disclosed. Some embodiments, allow the use of the generally smaller diameter co-radially constructed body (coated wires) to construct an active fixation lead, with an extendable/retractable fixation mechanism. Some embodiments use a connector assembly with an inner terminal ring, a terminal pin partially rotatably positioned within the annular inner terminal ring, and one or more resilient C-clips disposed within circumferential recesses. The resilient C-clips mechanically and electrically couple the inner terminal ring and the terminal ring while substantially limiting relative longitudinal translation of the terminal pin. In some embodiments, the connector assembly can be connected to an electrically inactive torque tube disposed longitudinally within the flexible body of the lead such that rotation of the terminal pin relative to the lead body causes rotation and longitudinal translation of a fixation helix relative to the body.

22 Claims, 9 Drawing Sheets

MRI SAFE, MULTIPOLAR ACTIVE FIXATION STIMULATION LEAD WITH CO-RADIAL CONSTRUCTION

CROSS-REFERENCE TO RELATED APPLICATION

This application claims priority to Provisional Application No. 61/291,553, filed Dec. 31, 2009, which is incorporated herein by reference in its entirety.

TECHNICAL FIELD

Various embodiments of the present invention generally relate to implantable medical devices. More specifically, embodiments of the present invention relate to MRI safe, multi-polar active fixation stimulation leads with co-radial construction.

BACKGROUND

When functioning properly, the human heart maintains its own intrinsic rhythm and is capable of pumping adequate blood throughout the body's circulatory system. However, some individuals have irregular cardiac rhythms, referred to as cardiac arrhythmias, which can result in diminished blood circulation and cardiac output. One manner of treating cardiac arrhythmias includes the use of a pulse generator (PG) such as a pacemaker, an implantable cardioverter defibrillator (ICD), or a cardiac resynchronization (CRT) device. Such devices are typically coupled to a number of conductive leads having one or more electrodes that can be used to deliver pacing therapy and/or electrical shocks to the heart. In atrio-ventricular (AV) pacing, for example, the leads are usually positioned in a ventricle and atrium of the heart, and are attached via lead terminal pins to a pacemaker or defibrillator which is implanted pectorally or in the abdomen.

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to radio frequency (RF) pulses of electromagnetic energy in a plane perpendicular to the magnetic field. The resultant electromagnetic energy from these pulses can be used to image the body tissue by measuring the relaxation properties of the excited atomic nuclei in the tissue. In some cases, imaging a patient's chest area may be clinically advantageous. In a chest MRI procedure, implanted pulse generators and leads may also be exposed to the applied electromagnetic fields.

SUMMARY

Various embodiments of MRI safe, multi-polar active fixation stimulation leads with co-radial construction are disclosed. In Example 1, an electrical lead comprises a flexible body having a length, a proximal region with a proximal end, and a distal region with a distal end. The electrical lead also includes an extendable and retractable fixation helix assembly coupled to the distal end of the lead body. The extendable and retractable fixation helix includes a housing, a coupler disposed within the housing having a proximal portion and a distal portion, a fixation helix fixedly secured to the distal portion of the coupler, and a guide structure within the housing operable to cause the coupler and the fixation helix to translate longitudinally upon rotation of the coupler and fixation helix relative to the housing. The lead can include a connector assembly coupled to the proximal end of the flexible body to electrically and mechanically connect the electrical lead to an implantable pulse generator. The connector assembly can include an annular inner terminal ring having an outer surface, an inner surface, and a circumferential recess extending from the inner surface toward the outer surface. In addition, the connector assembly can include a terminal pin partially rotatably positioned within the annular inner terminal ring having a proximal end, a distal end, and circumferential recess substantially aligned with the circumferential recess of the annular inner terminal ring. A resilient C-clip can be disposed within the circumferential recesses of the annular inner terminal ring and the terminal pin. The C-clip can mechanically and electrically couple the annular inner terminal ring and the terminal ring and being configured to substantially limit relative longitudinal translation of the terminal pin and the annular inner terminal ring while allowing the terminal pin to rotate relative to the annular inner terminal ring. An outer terminal ring can be disposed circumferentially around at least a portion of the annular inner terminal ring. In addition, an insulating layer between the outer terminal ring and the annular inner terminal rings may be present. In some cases, an electrically inactive torque tube can be disposed longitudinally within the flexible body and mechanically connected to the distal end of the terminal pin and to the proximal portion of the coupler such that rotation of the terminal pin relative to the flexible body causes rotation and longitudinal translation of the coupler and the fixation helix relative to the flexible body. Also, the electrical lead can include a multi-filar conductor coil disposed longitudinally within the flexible body, the multi-filar conductor coil including at least a first filar defining a first conduction path and at least a second filar defining a second conductive path electrically isolated from the first conductive path, the first and second filars co-radially wound to form the multi-filar conductor coil. The first filar can be electrically coupled to the annular inner terminal ring and thereby electrically coupled to the terminal pin through the resilient C-clip. The second filar can be electrically coupled to the outer terminal ring. The conductor coil can be substantially fixed relative to the flexible body. In some cases, the first and second filars can be dimensioned to have an impedance of about several thousand ohms or higher when exposed to an external magnetic field characterized by 1.5 Tesla to 3.0 Tesla. The electrical lead can also include a first electrode coupled to the flexible body in the distal region and electrically coupled to the first filar. Also, a second electrode can be coupled to the flexible body in the distal region and electrically coupled to the second filar.

In Example 2, the electrical lead according to Example 1, wherein the coupler includes a first cylindrically section on the proximal end with a proximal diameter and a second cylindrically section on the distal end with a distal diameter, wherein the distal diameter is greater than the proximal diameter.

In Example 3, the electrical lead according to Example 1 or 2, wherein the resilient C-clip has a width between approximately $25/1000$ of an inch to approximately $5/1000$ of an inch and the resilient C-clip has an average diameter between approximately $20/1000$ of an inch to approximately $80/1000$ of an inch.

In Example 4, the electrical lead according to Example 3, wherein the terminal pin has a terminal pin length of approximately $200/1000$ of an inch and an average diameter of between approximately $5/1000$ of an inch to approximately $90/1000$ of an inch.

In Example 5, the electrical lead according to Example 1, 2, 3, or 4, wherein the fixation helix is not electrically active and is designed to fixate the electrical lead to tissue within a heart.

In Example 6, the electrical lead according to Example 1, 2, 3, 4 or 5, wherein the multi-filar conductor coil is a 2-filar coil.

In Example 7, the electrical lead according to Example 1, 2, 3, 4, 5 or 6, wherein the electrically inactive torque tube has an outer diameter between approximately $25/1000$ of an inch and approximately $45/1000$ of an inch and an inner diameter between approximately $15/1000$ of an inch and approximately $25/1000$ of an inch.

In Example 8, the electrical lead according to Example 1, 2, 3, 4, 5, 6 or 7, wherein the electrically inactive torque tube includes two filaments wound in opposite directions to provide an even torque distribution relative to winding direction.

In Example 9, the electrical lead according to Example 8, wherein the electrically inactive torque tube creates an inner lumen with a smooth surface allowing insertion of a stylet or guidewire.

In Example 10, the electrical lead according to Example 1, 2, 3, 4, 5 6, 7, 8 or 9, wherein the wherein the multi-filar conductor coil is radially disposed about the electrically inactive torque tube along a substantial portion of the length of the flexible body.

In Example 11, the electrical lead according to Example 1, 2, 3, 4, 5 6, 7, 8, 9 or 10, wherein the resilient C-clip is made with a combination of one or more of gold, stainless steel, platinum, palladium, or protactinium.

In Example 12, a medical lead can convey electrical signals between a heart and a pulse generator. The medical lead comprises a flexible body having a length, a proximal region with a proximal end, and a distal region with a distal end. In addition, the medical lead can include a connector assembly coupled to the proximal end of the flexible body to electrically and mechanically connect the medical lead to an implantable pulse generator. The connector assembly can include an annular inner terminal ring with having an outer surface, an inner surface, and two terminal ring circumferential recesses extending from the inner surface toward the outer surface. Also, the connector assembly can include a terminal pin that is partially rotatably positioned within the annular inner terminal ring, the terminal pin having a proximal end, a distal end, and to terminal pin circumferential recesses substantially aligned with the terminal ring circumferential recesses. A first resilent C-clip and a second resilent C-clip can be each disposed between one of the terminal ring circumferential recesses and one of the terminal pin circumferential recesses to mechanically and electrically couple the annular inner terminal ring and the terminal pin. The first resilent C-clip and the second resilent C-clip can substantially limit the relative longitudinal translation of the terminal pin and the annular inner terminal ring while allowing the terminal pin to rotate. In addition, an annular outer terminal ring can be disposed circumferentially around at least a portion of the annular inner terminal ring. The medical lead can also include a torque tube disposed longitudinally within the flexible body and mechanically connected to a distal end of the terminal pin. When the terminal pin rotates, the torque tube drives a fixation helix coupled to a distal end of the torque tube. In addition, the medical lead can include a first electrode and a second electrode each coupled to the flexible body in the distal region. Also, a conductor coil can be disposed longitudinally within the flexible body with at least two electrically isolated conductive paths. One of the at least two electrically isolated conductive path can couple the first electrode to the annular inner terminal ring and thereby to the terminal pin through the first resilient C-clip and the second resilient C-clip.

One of the at least two electrically isolated conductive paths can couple the second electrode to the outer terminal ring. The conductor coil can be substantially fixed relative to the flexible body and designed to have an impedance of several thousand ohms or higher when exposed to an external magnetic field characterized by 1.5 Tesla to 3.0 Tesla.

In Example 13, the medical lead according to Example 12, wherein the fixation helix coupled to the distal end of the torque tube is part of a fixation assembly that includes a housing with a distal region and a proximal region, wherein the proximal region is fixedly coupled to the distal end of the flexible body and is electrically connected to the conductor coil. Furthermore, the fixation assembly can include a coupler rotatably disposed within the housing and the coupler having a distal end and a proximal end connected to the torque tube. The fixation helix can be fixedly secured to the distal end of the coupler. A guide element can be connected to or integral with the housing, wherein the guide element includes an engaging surface and a proximal bearing surface. The engaging surface can be configured to engage the fixation helix and allow the coupler to translate longitudinally when the fixation helix is rotated against the engaging surface. The longitudinal translation of the coupler relative to the housing is limited by the distal end of the coupler contacting the proximal bearing surface of the guide element.

In Example 14, the medical lead according to Example 12 or 13, wherein the two terminal ring circumferential recesses extend radially around an entire circumference of the annular inner terminal ring.

In Example 15, the medical lead according to Example 12, 13, or 14, wherein the two terminal ring circumferential recesses extend radially around only a portion of the circumference of the annular inner terminal ring and are radially offset by 180 degrees.

In Example 16, the medical lead according to Example 12, 13, 14 or 15, wherein the conductor coil includes at least two filars co-radially wound to form the conductor coil.

In Example 17, the medical lead according to Example 12, 13, 14, 15, or 16, further including one or more layers of insulation between the terminal pin and the inner conductor ring housing.

In Example 18, the medical lead according to Example 12, 13, 14, 15, 16 or 17, wherein the torque tube includes two filaments wound in opposite directions to provide an even torque distribution relative to a winding direction.

In Example 19, the medical lead according to Example 12, 13, 14, 15, 16, 17 or 18, wherein the first spring C-clip and the second spring C-clip have widths between approximately $25/1000$ of an inch to approximately $50/1000$ of an inch and average diameters between approximately $20/1000$ of an inch to approximately $80/1000$ of an inch.

In Example 20, an electrical lead comprises a flexible body having a length, a proximal region with a proximal end, and a distal region. In addition, the electrical lead can include an extendable and retractable fixation helix assembly coupled to the distal end of the lead body. The extendable and retractable fixation helix assembly can include a housing, a coupler disposed within the housing having a proximal portion and a distal portion, a fixation helix fixedly secured to the distal portion of the coupler, and a guide structure within the housing operable to cause the coupler and the fixation helix to translate longitudinally upon rotation of the coupler and fixation helix relative to the housing. The electrical lead can also include a connector assembly coupled to the proximal end of the flexible body of the electrical lead to electrically and mechanically connect the electrical lead to an implantable pulse generator. The connector assembly can include an annular inner terminal ring having a circumference, an outer surface, an inner surface, and one or more terminal ring circumferential recess extending from the inner surface toward the outer surface around a portion of the circumference. Also, the connector assembly can include a terminal pin partially rotatably positioned within the annular inner terminal ring having a proximal end, a distal end, and one or more terminal pin circumferential recesses substantially aligned with the circumferential recesses of the annular inner terminal ring. One or more resilient C-clips can be disposed within the terminal ring circumferential recesses and the terminal pin circumferential recesses of annular inner terminal ring and the terminal pin. The one or more resilient C-clips can mechanically and electrically couple the annular inner terminal ring and the terminal ring. Also, the resilient C-clips can substantially limit relative longitudinal translation of the terminal pin and the annular inner terminal ring while allowing the terminal pin to rotate relative to the annular inner terminal ring. The lead can also include an outer terminal ring disposed circumferentially around at least a portion of the annular inner terminal ring. Furthermore, the lead can include an electrically inactive torque tube disposed longitudinally within the flexible body and mechanically connected to the distal end of the terminal pin and to the proximal portion of the coupler such that rotation of the terminal pin relative to the lead body causes rotation and longitudinal translation of the coupler and the fixation helix relative to the flexible body. In some cases, the lead can include a first electrode and a second electrode coupled to the flexible body in the distal region. Also, the lead may include a multi-path conductor coil disposed longitudinally within the flexible body. The multi-path conductor coil can include at least a first conduction path and at least a second conductive path electrically isolated from the first conductive path. The first conduction path can electrically couple the first electrode to the annular inner terminal ring and thereby the terminal pin through the one or more resilient C-clips. The second conduction path can electrically couple the second electrode to the outer terminal ring. In some cases, the multi-filar conductor coil can be substantially fixed relative to the flexible body. The multi-path conductor coil can have an impedance of several thousand ohms or greater when exposed to an external magnetic field characterized by 1.5 Tesla to 3.0 Tesla.

In Example 21, the electrical lead according to Example 20, wherein the one or more resilient C-clips have a width between approximately $25/1000$ of an inch to approximately $50/1000$ of an inch and wherein the one or more resilient C-clips have an average diameter between approximately $20/1000$ of an inch to approximately $80/1000$ of an inch.

In Example 22, the electrical lead according to Example 20 or 21, further including one or more layers of insulation between the terminal pin and the inner conductor ring housing.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
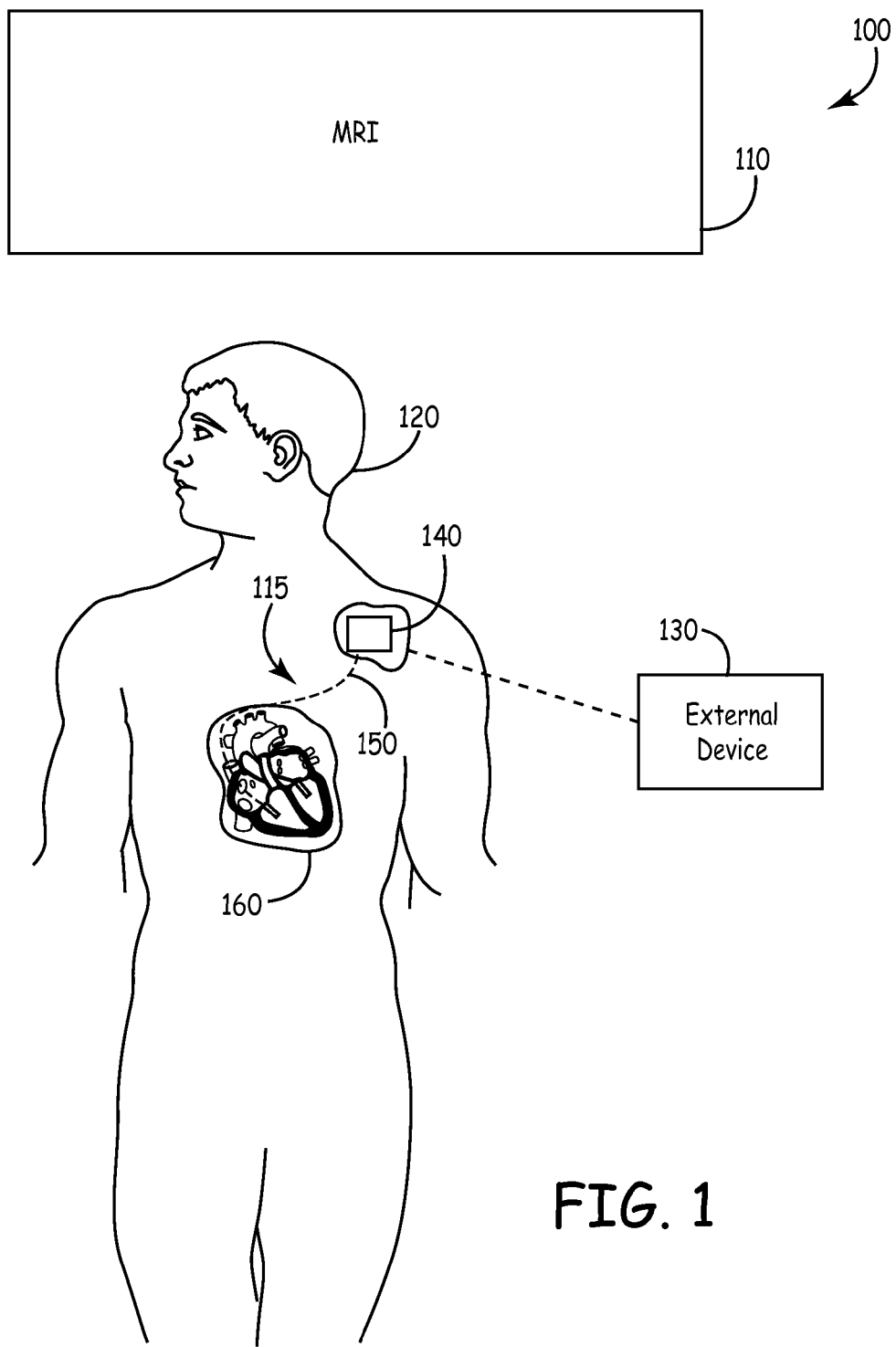
FIG. 1 is a schematic illustration of a medical system including an MRI scanner, and an implantable cardiac rhythm management system implanted within a torso of a human patient according to various embodiments of the present invention.

The drawings have not necessarily been drawn to scale. For example, the dimensions of some of the elements in the figures may be expanded or reduced to help improve the understanding of the embodiments of the present invention. While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

An implantable pulse generator (PG) such as a pacemaker, an implantable cardioverter defibrillator (ICD), or a cardiac resynchronization (CRT) device is typically implanted in the pectoral region of a patient. In some cases, multi-polar leads can be used with one or more electrodes. The lead may extend from the PG into an atrium and/or ventricle of the patient's heart. In the case of epicardial leads, for example, the electrodes are attached to an external surface of the patient's heart. The PG can provide pacing capability to the patient's heart and/or a high voltage shocking therapy to convert patient's heart from fibrillation to normal heart function.

Bipolar or multi-polar leads can be constructed in one of several ways. For example, the leads may be coaxial, co-radial, or multi-lumen. Coaxial leads utilize conductors that are symmetrically positioned around each other in a generally concentric array. Co-radial leads can be constructed by utilizing individually insulated wires that are shaped into a conductor. The individually insulated wires serve to electrically isolate each conductor path, while maintaining a small overall diameter conductor. Multi-lumen construction utilizes insulation tubing with multiple lumens to isolate the conductors. Some lead constructions use combinations or variations on these three approaches. Of the three approaches, co-radial construction may allow for the smallest diameter designs. Small diameter is sometimes an important design consideration.

Leads generally utilize one of two fixation approaches—active fixation or passive fixation. Most pacemaker leads that are classed as active fixation leads, for example, utilize an extendable/retractable helix in the distal end of the lead, which serves as both the fixation method and the distal stimulation electrode.

Stimulation leads with extendable retraction mechanisms may be used to rapidly fixate electrodes in desired positions. Most are constructed with a co-axial approach (two coils and two insulators which are concentric. This allows one conductor to rotate relative to the other, allowing the fixation mechanism to advance or retract as needed. However, one of the challenges with co-radial construction is the development a lead design which has an extendable retraction helix, small body diameter and the utilization of the lead's terminal pin to move the helix (via terminal pin rotation).

In contrast to these traditional stimulation leads, various embodiments of the present invention allow the use of the generally smaller diameter co-radially constructed body (coated wires) to construct an active fixation lead, with an extendable/retractable fixation mechanism. In some embodiments, the lead may be bipolar. In other embodiments, the lead may have a greater number of conductors. In various embodiments, a mechanism is provided that allows a co-radial type conductor to provide electrical continuity with the distal electrodes, the use of a conventional terminal construction, and allows for the terminal pin of the lead to rotate thereby driving the distal helix to extend and retract on demand. In addition, various embodiments of the present invention can be applied to IS-1 and IS-4 connector type active fixation lead designs in addition to other connector types.

As explained in further detail below, various embodiments of the present invention relate to new lead designs advantageously adapted for operation in a magnetic resonance imaging (MRI) environment. In some embodiments, the leads include unique coil conductors configured to provide suitable electrical performance for pacing therapy and to minimize the lead's reaction to applied electromagnetic energy during MRI procedures. For example, some embodiments increase the average diameter of the conductor coil, while maintaining a suitable pitch, to produce less lead electrode heating in an MRI environment as compared to traditional leads. In one embodiment, the coil pitch is minimized using a wire with a diameter less than $6/1000$ of an inch.

In the following description, for the purposes of explanation, numerous specific details are set forth in order to provide a thorough understanding of embodiments of the present invention. It will be apparent, however, to one skilled in the art that embodiments of the present invention may be practiced without some of these specific details.

While, for convenience, some embodiments are described with reference to implantable medical devices (IMDs) in the presence of MRI scanners. Embodiments of the present invention may be applicable to various other physiological measurements, treatments, IMD devices, various lead types (e.g., bradycardia/pacing leads, defibrillation leads, cardiac resynchronization therapy leads, and neurostimulation leads), and other medical applications in which implanted conductive leads are exposed to time varying magnetic fields. As such, the applications discussed herein are not intended to be limiting, but instead exemplary.

FIG. 1 is a schematic illustration of a medical system 100 including an MRI scanner 110, an implantable cardiac rhythm management (CRM) system 115 implanted within a torso of a human patient 120, and one or more external device(s) 130 according to various embodiments. The external device(s) 130 are capable of communicating with the CRM system 115 implanted within the patient 120. In the embodiment shown in FIG. 1, the CRM system 115 includes a pulse generator (PG) 140 and a lead 150. During normal device operation, the PG 140 is configured to deliver electrical therapeutic stimulus to the patient's heart 160 for providing tachycardia ventricular fibrillation, anti-bradycardia pacing, anti-tachycardia pacing, and/or other types of therapy.

Thus, in the illustrated embodiment, the PG 140 can be a device such as an ICD, cardiac resynchronization therapy device with defibrillation capabilities (a CRT-D device), or a comparable device. The PG 140 can be implanted pectorally within the body, typically at a location such as in the patient's chest. In some embodiments, PG 140 can be implanted in or near the abdomen.

The external device(s) 130 may be a local or remote terminal or other device (e.g., a computing device and/or programming device), operable to communicate with the PG 140 from a location outside of the patient's body. According to various embodiments, external device 130 can be any device external to the patient's body that is telemetry enabled and capable of communicating with the PG 140. Examples of external devices can include, but are not limited to, programmers (PRM), in-home monitoring devices, personal computers with telemetry devices, MRI scanner with a telemetry device, manufacturing test equipment, or wands. In some embodiments, the PG 140 communicates with the remote terminal 130 via a wireless communication interface. Examples of wireless communication interfaces can include, but are not limited to, radio frequency (RF), inductive, and acoustic telemetry interfaces.

Figure 2A:
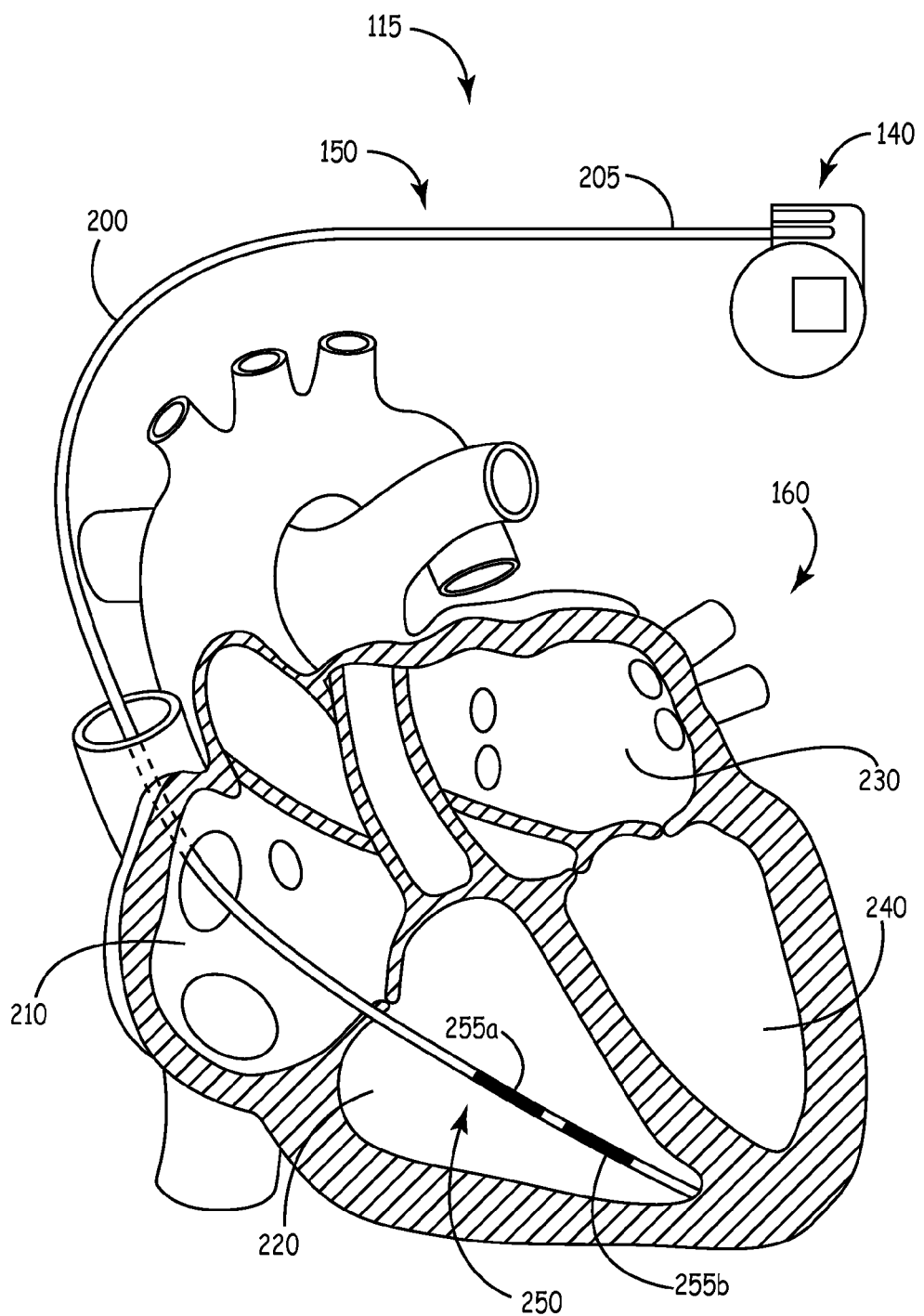
FIG. 2A is a schematic view of an illustrative pulse generator and lead implanted within the body of a patient which may be used in accordance with some embodiments of the present invention.

FIG. 2A is a more detailed schematic view of the CRM system 115 including the illustrative PG 140 equipped with the lead 150 implanted within the body of a patient. In the embodiments depicted, CRM system 115 includes PG 140 implanted near the patient's heart 160 and lead 150 having a distal portion implanted with the patient's heart 160. As can be seen in FIG. 2A, the heart 160 includes a right atrium 210, a right ventricle 220, a left atrium 230, and a left ventricle 240.

The lead 150 has a flexible body 200 including a proximal region 205 and a distal region 250. As shown, the lead 150 is coupled to the PG 140, and the distal region 250 of the lead body 200, at least partially implanted at a desired location within the right ventricle 220. As illustrated in FIG. 2A, the lead 150 includes two electrodes 255a and 255b along the distal region 250, such that when implanted as shown in FIG. 2A, it is positioned within the right ventricle 220. However, other embodiments may have more or less electrodes. As explained and illustrated in further detail below, the lead 150 includes one or more electrical conductor coils within the lead body 250 (not visible in FIG. 2A) electrically coupling the electrode 255 to circuitry and other electrical components within the PG 140 for transmitting intrinsic cardiac signals from the heart 160 to the PG 140 and also for transmitting electrical shocks or low-voltage pacing stimuli to the heart 160 via the electrode 255.

Although the illustrative embodiment depicts only a single lead 150 inserted into the patient's heart 160, in other embodiments multiple leads can be utilized so as to electrically stimulate other areas of the heart 160. In some embodiments, for example, the distal portion of a second lead (not shown) may be implanted in the right atrium 210. In addition, or in lieu of, another lead may be implanted at the left side of the heart 160 (e.g., in the coronary veins, the left ventricle, etc.) to stimulate the left side of the heart 160. Other types of leads such as epicardial leads may also be utilized in addition to, or in lieu of, the lead 150 depicted in FIGS. 1-2.

During operation, the lead 150 conveys electrical signals between the heart 160 and the PG 140. For example, in those embodiments where the PG 140 has pacing capabilities, the lead 150 can be utilized to deliver electrical therapeutic stimulus for pacing the heart 160. In those embodiments where the PG 140 is an ICD, the lead 150 can be utilized to deliver high voltage electric shocks to the heart 160 via the electrodes 255a and 255b in response to an event such as a ventricular fibrillation. In some embodiments, the PG 140 includes both pacing and defibrillation capabilities.

Figure 2B:
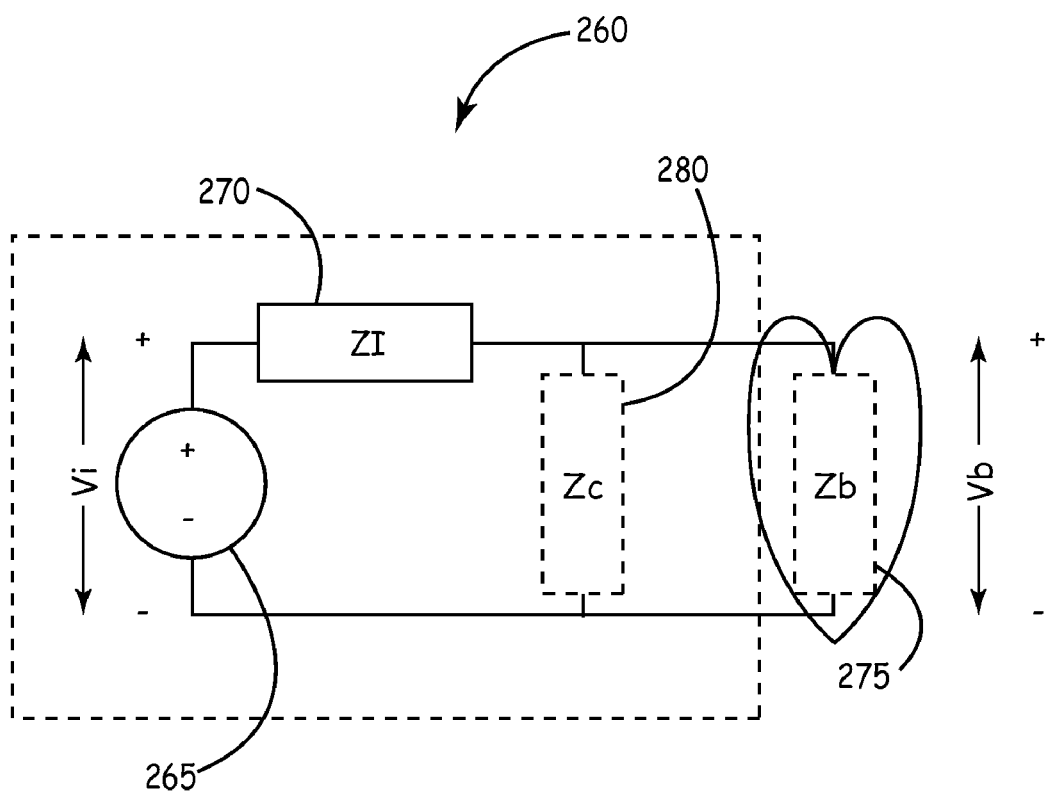
FIG. 2B is a schematic view showing a simplified equivalence circuit for the lead of FIG. 2A.

FIG. 2B is a schematic view showing a simplified equivalence circuit 260 for the lead 150 of FIG. 2A, representing the RF energy picked up on the lead 150 from RF electromagnetic energy produced by an MRI scanner. As shown in FIG. 2B, voltage (Vi) 265 in the circuit 260 represents an equivalent source of energy picked up by the lead 150 from the MRI scanner. During magnetic resonance imaging, the length of the lead 150 functions similar to an antenna, receiving the RF energy that is transmitted into the body from the MRI scanner. Voltage (Vi) 265 in FIG. 2B may represent, for example, the resultant voltage received by the lead 150 from the RF energy. The RF energy picked up by the lead 150 may result, for example, from the rotating RF magnetic field produced by an MRI scanner, which generates an electric field in the plane perpendicular to the rotating magnetic field vector in conductive tissues. The tangential components of these electric fields along the length of the lead 150 couple to the lead 150. The voltage (Vi) 265 is thus equal to the integration of the tangential electric field (i.e., the line integral of the electric field) along the length of the lead 150.

The Zl parameter 270 in the circuit 260 represents the equivalent impedance exhibited by the lead 150 at the RF frequency of the MRI scanner. The impedance value Zl 270 may represent, for example, the inductance or the equivalent impedance resulting from the parallel inductance and the coil turn by turn capacitance exhibited by the lead 150 at an RF frequency of 64 MHz for a 1.5 Tesla MRI scanner, or at an RF frequency of 128 MHz for a 3 Tesla MRI scanner. The impedance Zl of the lead 150 is a complex quantity having a real part (i.e., resistance) and an imaginary part (i.e., reactance).

Zb 275 in the circuit 260 may represent the impedance of the body tissue at the point of lead contact. Zc 280, in turn, may represent the capacitive coupling of the lead 150 to surrounding body tissue along the length of the lead 150, which may provide a path for the high frequency current (energy) to leak into the surrounding tissue at the RF frequency of the MRI scanner. Minimizing the absorbed energy (represented by source Vi 265) reduces the energy that is transferred to the body tissue at the point of lead contact with the body tissue.

As can be further seen in FIG. 2B, the lead 150 has some amount of leakage into the surrounding tissue at the RF frequency of the MRI scanner. As further indicated by 275, there is also an impedance at the point of contact of the lead electrode(s) 255 to the surrounding body tissue within the heart 160. The resulting voltage Vb delivered to the body tissue may be related by the following formula:

$$Vb = Vi \, Zbe/(Zbe-FZl), \text{ where } Zbe = Zb \text{ in parallel with } Zc.$$

The temperature at the tip of the lead 150 where contact is typically made to the surrounding tissue is related in part to the power dissipated at 275 (i.e., at "Zb"), which, in turn, is related to the square of Vb. To minimize temperature rises resulting from the power dissipated at 275, it is thus desirable to minimize Vi (265) and Zc (280) while also maximizing the impedance Zl (270) of the lead 150. In some embodiments, the impedance Zl (270) of the lead 150 can be increased at the RF frequency of the MRI scanner, which aids in reducing the energy dissipated into the surrounding body tissue at the point of contact 275.

In the various embodiments described in further detail below, the impedance of the lead 150 can be increased by adding inductance to the lead 150 and/or by a suitable construction technique. For example, in various embodiments, the inductance of the lead 150 is increased by increasing the mean diameter of the conductor coil(s) and/or by decreasing the pitch of the conductor coil(s) used to supply electrical energy to the electrode(s) 255. Decreasing the coil pitch may result in increasing capacitance between successive turns of the coil (i.e., coil turn by turn capacitance). The parallel combination of inductance (from the helical shape of the coil) and the turn by turn capacitance constitutes a resonance circuit. For a helically coiled lead construction, if the resonance frequency of the lead is above the RF frequency of the MRI, then the helical coil acts as an inductor. For an inductor, increasing the cross section of the coil area and/or reducing the coil pitch increases the inductance and, as a result, increases the impedance of the lead 150.

Figure 3:
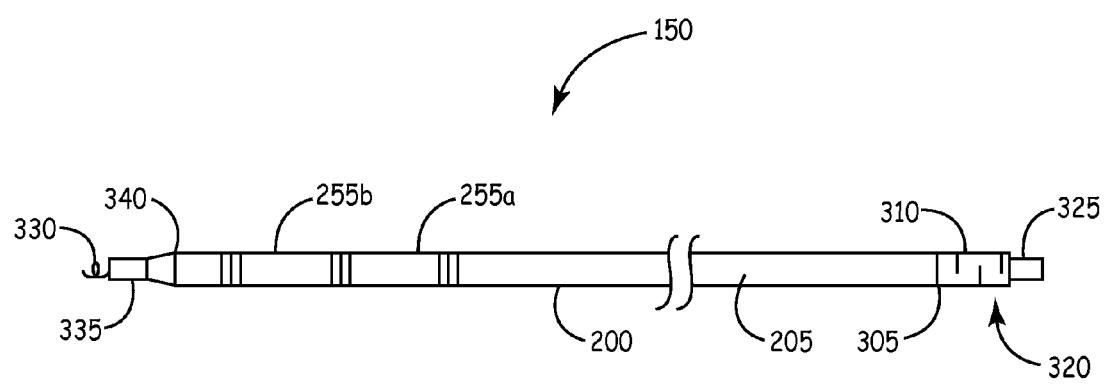
FIG. 3 is schematic illustrating an exemplary lead that may be used in accordance with one or more embodiments of the present invention.

FIG. 3 schematically illustrates in further detail the exemplary lead 150 that may be used in accordance with one or more embodiments of the present invention. As shown in FIG. 3, the lead body 200 includes a proximal end 305 at the end of proximal region 205, and the lead 150 further includes a connector assembly 310 coupled to the proximal end 305 of the lead body, coil electrodes 255a and 255b. Depending on the functional requirements of the IMD 140 (see FIG. 1), and the therapeutic needs of the patient, the distal region may include additional shocking coils (not shown) and/or pace/sense electrodes. For example, in some embodiments, the pair of coil electrodes 255a and 255b can be used to function as shocking electrodes for providing a defibrillation shock to the heart 160.

In the illustrated embodiment, the connector assembly 310 includes a connector body 320 and a terminal pin 325. The connector assembly 310 is coupled to the lead body and can be configured to mechanically and electrically couple the lead to a header on PG 140 (see FIG. 1 and FIG. 2). In various embodiments, the terminal pin 325 extends proximally from the connector body 320 and in some embodiments is coupled to an inner conductor coil (not shown in FIG. 3) that extends longitudinally through the lead body 200 to one or more pace/sense electrodes, shocking electrodes, or ring electrodes. In some embodiments, the pace/sense electrode(s) can be a tip electrode located at the distal-most extremity of the lead 150, and can be fixed relative to the lead body 200 such that the lead 150 is considered a passive-fixation lead. In other embodiments, the lead 150 may include additional pace/sense electrodes located more proximally along the lead 150. In some embodiments, the terminal pin 325 can include an aperture extending therethrough communicating with a lumen defined by the inner conductor coil in order to accommodate a guide wire or an insertion stylet.

In the illustrated embodiment, the pace/sense electrode is in the form of an electrically active fixation helix 330 at the distal end of the lead 150. In such embodiments, the pace/sense electrode 330 can be an extendable/retractable helix supported by a mechanism to facilitate longitudinal translation of the helix relative to the lead body as the helix is rotated. In those embodiments, the terminal pin 325 may be rotatable relative to the connector body 320 and the lead body 200 such that rotation of the terminal pin 325 relative to the lead body 200 causes the inner conductor coil, and in turn, the helical pace/sense electrode 330 to rotate and translate longitudinally relative to the lead body 200.

The pace/sense electrode (whether a solid tip electrode as described above or an active-fixation helix such as shown in FIG. 3) can be made of any suitable electrically conductive material such as Elgiloy, MP35N, tungsten, tantalum, iridium, platinum, titanium, palladium, stainless steel, as well as alloys of any of these materials.

Figure 4A:
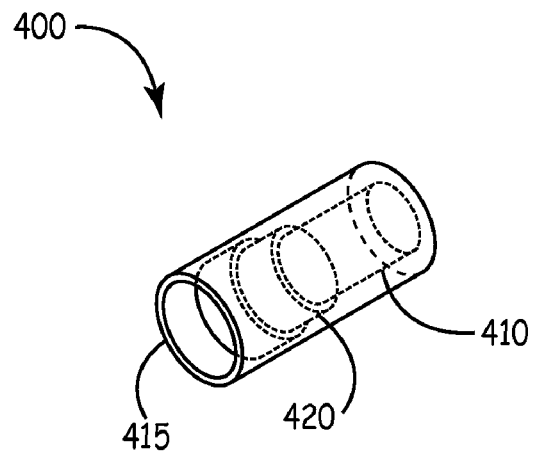
FIGS. 4A-4C are schematic illustrations showing an annular inner terminal ring, a terminal pin, and a resilient C-clip that can be used in a connector assembly according to some embodiments of the present invention.
Figure 4B:
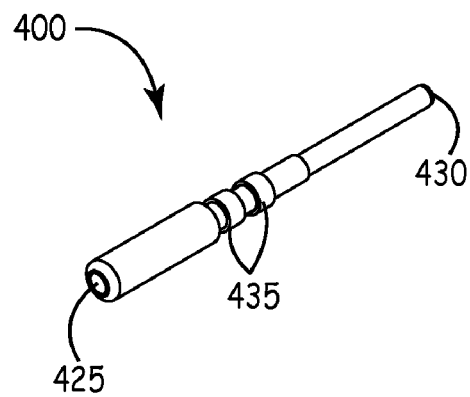
Figure 4C:
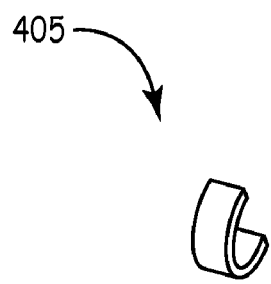

As described above, connector assembly 310 can be coupled to the proximal end of the flexible body 200 can electrically and mechanically connect the lead to an implantable PG. FIGS. 4A-4C illustrate annular inner terminal ring 400, terminal pin 325, and a resilient C-clip 405 that can be used in accordance with some embodiments in connector assembly 310.

FIG. 4A illustrates a partial cut away view an annular inner terminal ring 400 that can be used in accordance with various embodiments of the present invention. Annular inner terminal ring 400 can have an outer surface 410, an inner surface 415, and one or more circumferential recesses 420 extending from the inner surface toward the outer surface. FIG. 4B illustrates a terminal pin 325 that can be used in accordance with some embodiments of the present invention. As illustrated in FIG. 4B, terminal pin 325 can have a proximal end 425, a distal end 430, and one or more circumferential recess 435 substantially aligned with the circumferential recess of the annular inner terminal ring. Terminal pin 325 can be partially rotatably positioned within the annular inner terminal ring.

Resilient C-clip 405, illustrated in FIG. 4C, can then be disposed within the circumferential recesses of annular inner terminal ring and the terminal pin. The resilient C-clip 405 then mechanically and electrically couples the annular inner terminal ring and the terminal ring while substantially limiting relative longitudinal translation of the terminal pin and the annular inner terminal ring. In addition, resilient C-clip 405 allows the terminal pin to rotate relative to the annular inner terminal ring 400.

In some embodiments, the resilient C-clip can have a width between approximately $25/1000$ of an inch to approximately $50/1000$ of an inch. In one or more embodiments, the resilient C-clip can have an average diameter between approximately $20/1000$ of an inch to approximately $80/1000$ of an inch. According to various embodiments, the resilient C-clip can be made with a combination of one or more materials such as, but not limited to, gold, stainless steel, platinum, palladium, or protactinium.

In accordance with various embodiments, there may be two terminal ring circumferential recesses 420 that extend radially around an entire circumference of the annular inner terminal ring 400. In some embodiments, the corresponding circumferential recesses 435 of the terminal pin 325 may also extend radially around an entire circumference of the terminal pin 325. The circumferential recesses, in some embodiments, may not extend radially around the entire circumference of the terminal pin 325 and/or the annular inner terminal ring 400. For example, in some embodiments, one or more of the circumferential recesses 435 may extend only half way (i.e., 180 degrees) around the circumference of the terminal pin 325 and/or the annular inner terminal ring 400. In addition, in some embodiments with two or more circumferential recesses that extend only partially, they may be radially offset (e.g., by 180 degrees) to allow for easier assembly and more reliable connections.

Figure 5A:
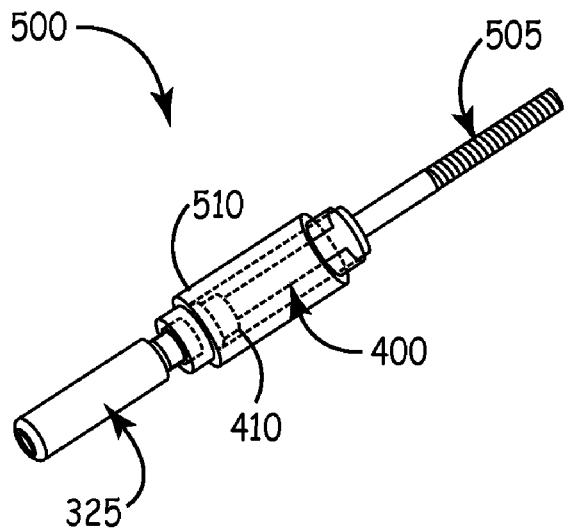
FIGS. 5A-5C are schematic illustrations showing the inner terminal ring, the terminal pin, and the resilient C-clip(s) assembled together according to one or more embodiments of the present invention.
Figure 5B:
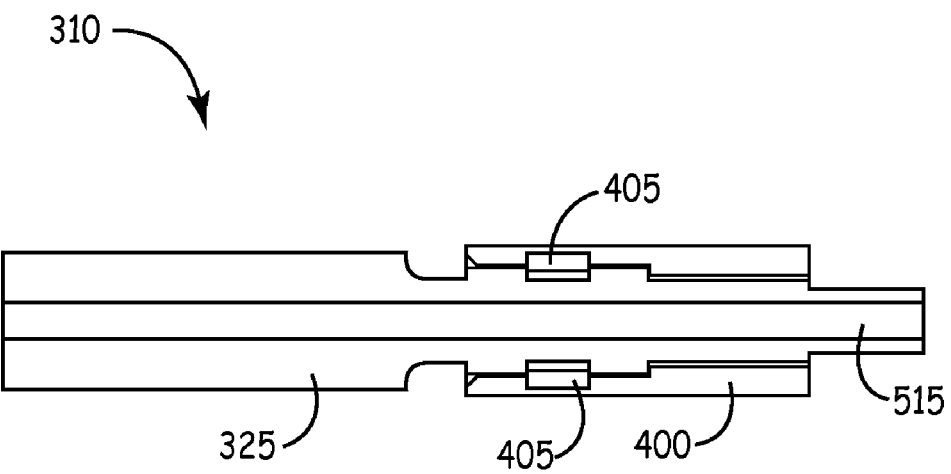
Figure 5C:
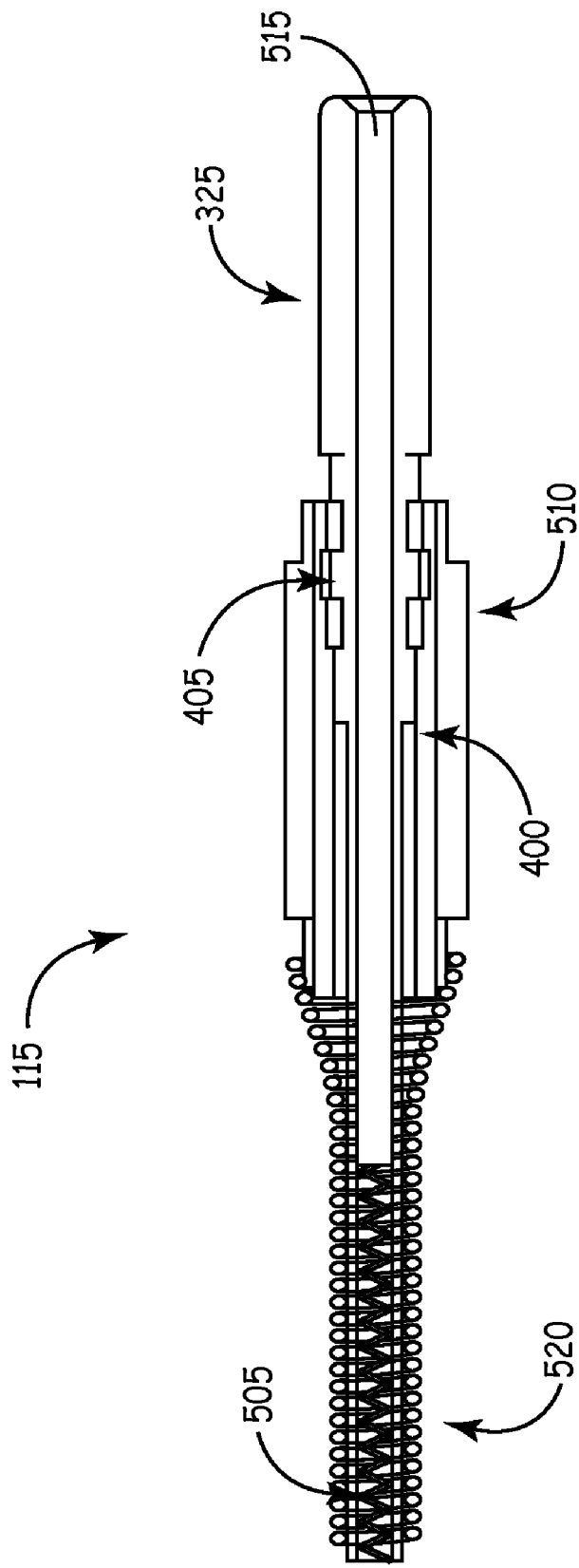

FIGS. 5A-5C illustrate how inner terminal ring 400, terminal pin 325, and resilient C-clip(s) 405 fit together according to one or more embodiments of the present invention. FIG. 5A shows a perspective view of a partial cutaway of the connector assembly 310 coupled to torque tube 505 which is radially disposed about an inner conductor coil. FIG. 5B, shows a longitudinal cross section of the connector assembly 310. FIG. 5C shows a longitudinal cross section of the connector assembly 310 coupled to torque tube 505 which is radially disposed within an inner multi-polar conductor coil.

FIG. 5A also shows an outer terminal ring 510 disposed circumferentially around at least a portion of the annular inner terminal ring 400. In some embodiments, an insulating layer between the outer terminal ring 510 and the annular inner terminal ring 400 may be used.

Figure 7:
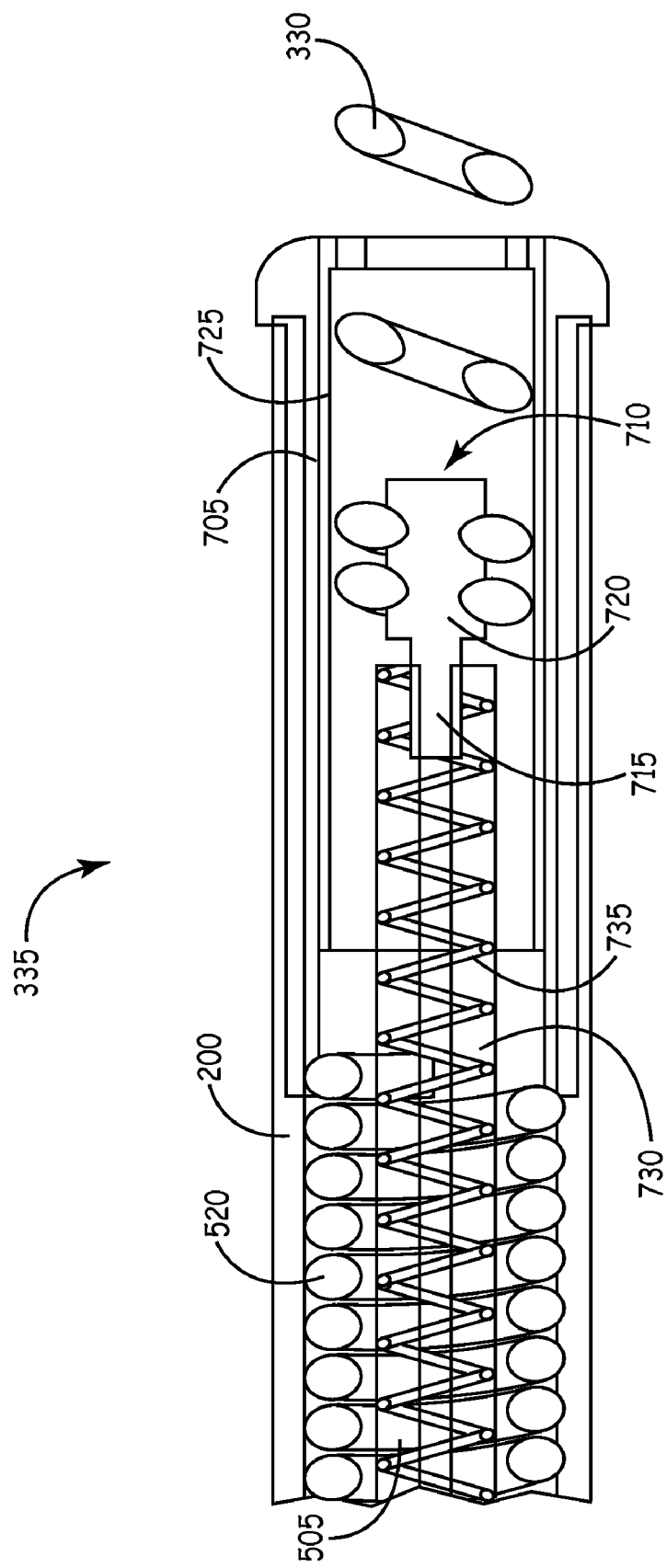
FIG. 7 is a longitudinal cross sectional view of extendable and retractable fixation helix assembly that can be used in accordance with some embodiments of the present invention.

The torque tube 505 can be electrically inactive and disposed longitudinally within the flexible body 200 in accordance with various embodiments of the present invention. As illustrated in FIG. 5A, the torque tube 505 can be mechanically connected to the distal end of the terminal pin 325 and to the proximal portion of a coupler (e.g., FIG. 7 shows a coupler within a fixation helix assembly) such that rotation of the terminal pin relative to the lead body causes rotation and longitudinal translation of the coupler and the fixation helix relative to the body of the fixation helix assembly. The torque tube 505 can have an outer diameter, according to various embodiments, between approximately $25/1000$ of an inch and approximately $45/1000$ of an inch and an inner diameter between approximately $15/1000$ of an inch and approximately $25/1000$ of an inch.

In some embodiments, the torque tube 505 includes two filaments wound in opposite directions to provide an even torque distribution relative to winding direction. The winding can create an inner lumen within the torque tube 505. In one or more embodiments, the inner lumen may have a smooth surface allowing for insertion of a stylet or guide wire. The guide wire may originate through lumen 515 (see, e.g., FIGS. 5B and 5C) in the connector assembly 310.

In some embodiments, a multi-filar conductor coil 520 can be disposed longitudinally within the flexible body 200 and around the torque tube 505. The conductor coil 520, in various embodiments, includes at least a first filar defining a first conduction path and at least a second filar defining a second conductive path electrically isolated from the first conductive path. The first and second filars can be co-radially wound to form the conductor coil 520. In some embodiments, the first filar can be electrically coupled to a first electrode that is coupled to the body in the distal region and the first filar can be electrically coupled to the annular inner terminal ring 400 and thereby electrically coupled to the terminal pin 325 through the resilient C-clip 405. The second filar can be electrically coupled to the outer terminal ring 510 and to a second electrode coupled to the body in the distal region. According to one or more embodiments, the conductor coil can be substantially fixed relative to the flexible body, the first and second filars dimensioned to have an impedance of several thousand ohms between conductors when in use and not in the presence of the MRI (i.e., no Tesla). In some embodiments, the first and second filars dimensioned to have an impedance of several thousand ohms or higher when exposed to an external magnetic field characterized by 1.5 Tesla to 3.0 Tesla. In addition, in some embodiments, various electrical parameters (e.g., impedance, inductance, capacitance, etc.) may be changed by changing the pitch, coil diameter, wire diameter, and other mechanical properties of the multi-filar conductor coil 520.

Figure 6:
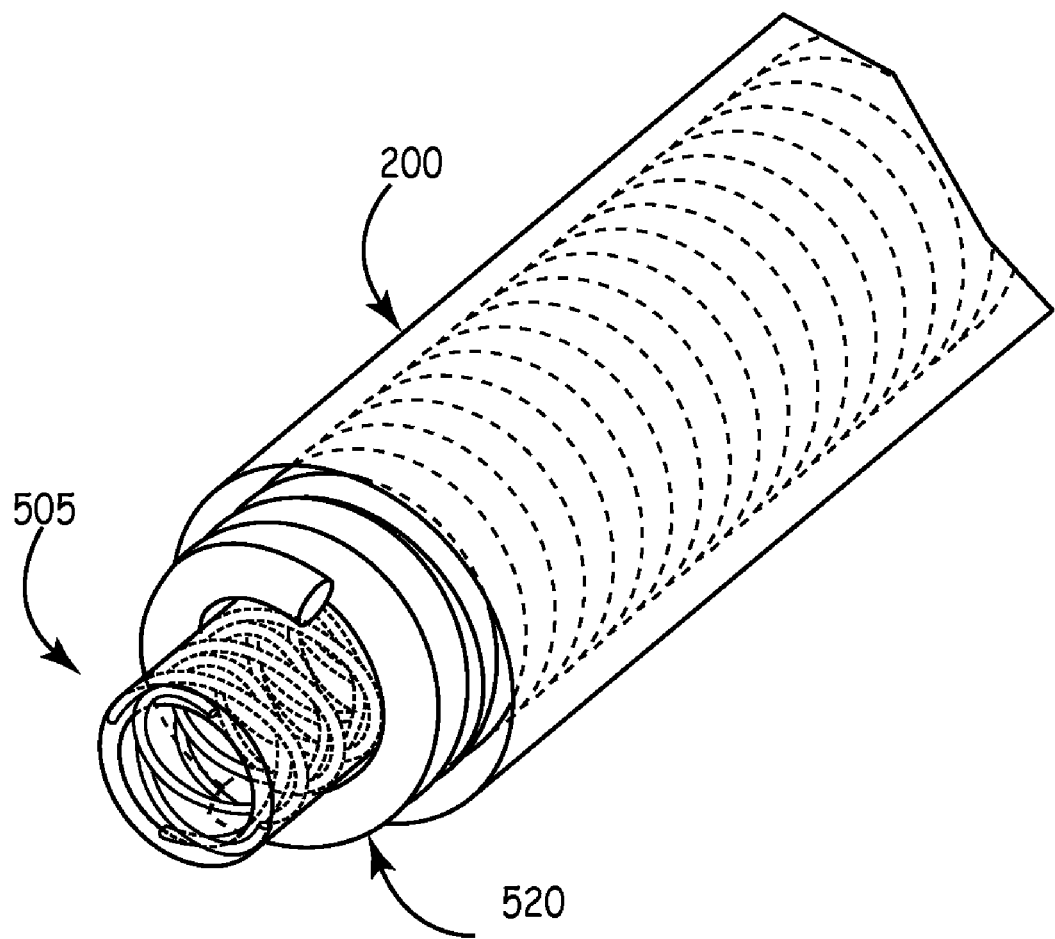
FIG. 6 is a partial cutaway illustration of a portion of lead in accordance with various embodiments of the present invention.

FIG. 6 illustrates a cutaway of a portion of lead 150 in accordance with various embodiments of the present invention. As illustrated in FIG. 6, the flexible body 200 is radially disposed about the conductor 520 which radially surrounds at least a portion of torque tube 505. According to some embodiments, the inner torque tube 505 controls the travel of the stiffening stylet and minimizes the chance of the stylet penetrating into the body from the lead central lumen regardless of the radius of the lead. This capturing of the stylet further allows freedom to increase the diameter of the conductor coil independently of stylet diameter, which in turn allows the conductor to increase in size/diameter which increased coil inductance and MRI performance. In at least one embodiment, the inner torque tube 505 allows traditional stylet spacing to be exceeded.

FIG. 7 shows a longitudinal cross section of the extendable and retractable fixation helix assembly 335 that can be used in accordance with some embodiments of the present invention. In some cases, the fixation helix 330 can be part of an extendable and retractable fixation helix assembly 335 that is coupled to the distal end 340 of the flexible lead body 200. In accordance with one or more embodiments, the fixation helix assembly 335 can include a housing 705 and a coupler 710 disposed within the housing 705 having a proximal portion and a distal portion. The fixation helix 330 can be fixedly secured to the distal portion of the coupler 710.

As illustrated in FIG. 7, the torque tube 505 can be mechanically connected to the proximal portion of the coupler 710 such that rotation of the terminal pin relative to the lead body causes rotation and longitudinal translation of the coupler 710 via torque tube 505. In some embodiments, coupler 710 can include a first cylindrically section 715 on the proximal end with a proximal diameter and a second cylindrically section 720 on the distal end with a distal diameter. In the embodiment illustrated, the distal diameter of coupler 710 is greater than the proximal diameter. In some embodiments, torque tube 505 includes two filaments 730 and 735 wound in opposite directions to provide an even torque distribution relative to winding direction. The torque tube 505 can be made out of a cut polymer tube in some embodiments of the present invention.

In some embodiments, the extendable and retractable fixation helix assembly 335 also includes a guide structure 725 within the housing 705. The guide structure 725 can be used to cause the coupler 710 and the fixation helix 330 to translate longitudinally upon rotation of the coupler 710 and fixation helix 330 relative to the housing. Various alternative mechanisms and techniques for providing extendable/retractable fixation helix assemblies (both electrically active and passive) can be used in accordance with various embodiments.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An electrical lead, comprising:
    a flexible body having a length, a proximal region with a proximal end, and a distal region with a distal end;
    an extendable and retractable fixation helix assembly coupled to the distal end of the lead body, including a housing, a coupler disposed within the housing having a proximal portion and a distal portion, a fixation helix fixedly secured to the distal portion of the coupler, and a guide structure within the housing operable to cause the coupler and the fixation helix to translate longitudinally upon rotation of the coupler and fixation helix relative to the housing;
    a connector assembly coupled to the proximal end of the flexible body to electrically and mechanically connect the electrical lead to an implantable pulse generator, wherein the connector assembly includes:
        an annular inner terminal ring having an outer surface, an inner surface, and a circumferential recess extending from the inner surface toward the outer surface;
        a terminal pin partially rotatably positioned within the annular inner terminal ring having a proximal end, a distal end, and circumferential recess substantially aligned with the circumferential recess of the annular inner terminal ring;
        a resilient C-clip disposed within the circumferential recesses of the annular inner terminal ring and the terminal pin, the C-clip mechanically and electrically coupling the annular inner terminal ring and the terminal pin and being configured to substantially limit relative longitudinal translation of the terminal pin and the annular inner terminal ring while allowing the terminal pin to rotate relative to the annular inner terminal ring;
        an outer terminal ring disposed circumferentially around at least a portion of the annular inner terminal ring;
        an insulating layer between the outer terminal ring and the annular inner terminal rings;
    an electrically inactive torque tube disposed longitudinally within the flexible body and mechanically connected to the distal end of the terminal pin and to the proximal portion of the coupler such that rotation of the terminal pin relative to the flexible body causes rotation and longitudinal translation of the coupler and the fixation helix relative to the flexible body;
    a multi-filar conductor coil disposed longitudinally within the flexible body, the multi-filar conductor coil including at least a first filar defining a first conduction path and at least a second filar defining a second conductive path electrically isolated from the first conductive path, the first and second filars co-radially wound to form the multi-filar conductor coil, the first filar electrically coupled to the annular inner terminal ring and thereby electrically coupled to the terminal pin through the resilient C-clip, the second filar electrically coupled to the outer terminal ring, the conductor coil being substantially fixed relative to the flexible body, the first and second filars dimensioned to have an impedance of about several thousand ohms or higher when exposed to an external magnetic field characterized by 1.5 Tesla to 3.0 Tesla;
    a first electrode coupled to the flexible body in the distal region and electrically coupled to the first filar; and
    a second electrode coupled to the flexible body in the distal region and electrically coupled to the second filar.

2. The electrical lead of claim 1, wherein the coupler includes a first cylindrically section on the proximal end with a proximal diameter and a second cylindrically section on the distal end with a distal diameter, wherein the distal diameter is greater than the proximal diameter.

3. The electrical lead of claim 1, wherein the resilient C-clip has a width between approximately $25/1000$ of an inch to approximately $50/1000$ of an inch and the resilient C-clip has an average diameter between approximately $20/1000$ of an inch to approximately $80/1000$ of an inch.

4. The electrical lead of claim 3, wherein the terminal pin has a terminal pin length of approximately $200/1000$ of an inch and an average diameter of between approximately 50/1000 of an inch to approximately 90/1000 of an inch.

5. The electrical lead of claim 1, wherein the fixation helix is not electrically active and is designed to fixate the electrical lead to tissue within a heart.

6. The electrical lead of claim 1, wherein the multi-filar conductor coil is a 2-filar coil.

7. The electrical lead of claim 1, wherein the electrically inactive torque tube has an outer diameter between approximately 25/1000 of an inch and approximately 45/1000 of an inch and an inner diameter between approximately 15/1000 of an inch and approximately 25/1000 of an inch.

8. The electrical lead of claim 1, wherein the electrically inactive torque tube includes two filaments wound in opposite directions to provide an even torque distribution relative to winding direction.

9. The electrical lead of claim 8, wherein the electrically inactive torque tube creates an inner lumen with a smooth surface allowing insertion of a stylet or guidewire.

10. The electrical lead of claim 1, wherein the wherein the multi-filar conductor coil is radially disposed about the electrically inactive torque tube along a substantial portion of the length of the flexible body.

11. The electrical lead of claim 1, wherein the resilient C-clip is made with a combination of one or more of gold, stainless steel, platinum, palladium, or protactinium.

12. A medical lead that can convey electrical signals between a heart and a pulse generator, the medical lead comprising:
  a flexible body having a length, a proximal region with a proximal end, and a distal region with a distal end;
  a connector assembly coupled to the proximal end of the flexible body to electrically and mechanically connect the medical lead to an implantable pulse generator, wherein the connector assembly includes:
    an annular inner terminal ring with having an outer surface, an inner surface, and two terminal ring circumferential recesses extending from the inner surface toward the outer surface;
    a terminal pin that is partially rotatably positioned within the annular inner terminal ring, the terminal pin having a proximal end, a distal end, and to terminal pin circumferential recesses substantially aligned with the terminal ring circumferential recesses;
    a first resilient C-clip and a second resilient C-clip each disposed between one of the terminal ring circumferential recesses and one of the terminal pin circumferential recesses to mechanically and electrically couple the annular inner terminal ring and the terminal pin, wherein the first resilient C-clip and the second resilient C-clip substantially limited the relative longitudinal translation of the terminal pin and the annular inner terminal ring while allowing the terminal pin to rotate;
    an annular outer terminal ring disposed circumferentially around at least a portion of the annular inner terminal ring;
  a torque tube disposed longitudinally within the flexible body and mechanically connected to a distal end of the terminal pin so that when the terminal pin rotates, the torque tube drives a fixation helix coupled to a distal end of the torque tube;
  a first electrode and a second electrode each coupled to the flexible body in the distal region; and
  a conductor coil disposed longitudinally within the flexible body, at least two electrically isolated conductive paths, wherein one of the at least two electrically isolated conductive path coupling the first electrode to the annular inner terminal ring and thereby to the terminal pin through the first resilient C-clip and the second resilient C-clip, one of the at least two electrically isolated conductive paths coupling the second electrode to the outer terminal ring, and wherein the conductor coil is substantially fixed relative to the flexible body and designed to have an impedance of several thousand ohms or higher when exposed to an external magnetic field characterized by 1.5 Tesla to 3.0 Tesla.

13. The medical lead of claim 12, wherein the fixation helix coupled to the distal end of the torque tube is part of a fixation assembly that includes:
  a housing with a distal region and a proximal region, wherein the proximal region is fixedly coupled to the distal end of the flexible body and is electrically connected to the conductor coil, and
  a coupler rotatably disposed within the housing and the coupler having a distal end and a proximal end connected to the torque tube;
  the fixation helix fixedly secured to the distal end of the coupler; and
  a guide element connected to or integral with the housing, wherein the guide element includes an engaging surface and a proximal bearing surface, wherein the engaging surface is configured to engage the fixation helix and allow the coupler to translate longitudinally when the fixation helix is rotated against the engaging surface; and
  wherein the longitudinal translation of the coupler relative to the housing is limited by the distal end of the coupler contacting the proximal bearing surface of the guide element.

14. The medical lead of claim 12, wherein the two terminal ring circumferential recesses extend radially around an entire circumference of the annular inner terminal ring.

15. The medical lead of claim 12, wherein the two terminal ring circumferential recesses extend radially around only a portion of the circumference of the annular inner terminal ring and are radially offset by 180 degrees.

16. The medical lead of claim 12, wherein the conductor coil includes at least two filars co-radially wound to form the conductor coil.

17. The medical lead of claim 12, further including one or more layers of insulation between the terminal pin and the inner conductor ring housing.

18. The medical lead of claim 12, wherein the torque tube includes two filaments wound in opposite directions to provide an even torque distribution relative to a winding direction.

19. The medical lead of claim 12, wherein the first spring C-clip and the second spring C-clip have widths between approximately 25/1000 of an inch to approximately 50/1000 of an inch and average diameters between approximately 20/1000 of an inch to approximately 80/1000 of an inch.

20. An electrical lead, comprising:
  a flexible body having a length, a proximal region with a proximal end, and a distal region;
  an extendable and retractable fixation helix assembly coupled to the distal end of the lead body, including a housing, a coupler disposed within the housing having a proximal portion and a distal portion, a fixation helix fixedly secured to the distal portion of the coupler, and a guide structure within the housing operable to cause the coupler and the fixation helix to translate longitudinally upon rotation of the coupler and fixation helix relative to the housing;

a connector assembly coupled to the proximal end of the flexible body of the electrical lead to electrically and mechanically connect the electrical lead to an implantable pulse generator, wherein the connector assembly includes:

an annular inner terminal ring having a circumference, an outer surface, an inner surface, and one or more terminal ring circumferential recess extending from the inner surface toward the outer surface around a portion of the circumference;

a terminal pin partially rotatably positioned within the annular inner terminal ring having a proximal end, a distal end, and one or more terminal pin circumferential recesses substantially aligned with the circumferential recesses of the annular inner terminal ring;

one or more resilient C-clips disposed within the terminal ring circumferential recesses and the terminal pin circumferential recesses of annular inner terminal ring and the terminal pin, the one or more resilient C-clips mechanically and electrically coupling the annular inner terminal ring and the terminal ring and substantially limiting relative longitudinal translation of the terminal pin and the annular inner terminal ring while allowing the terminal pin to rotate relative to the annular inner terminal ring;

an outer terminal ring disposed circumferentially around at least a portion of the annular inner terminal ring;

an electrically inactive torque tube disposed longitudinally within the flexible body and mechanically connected to the distal end of the terminal pin and to the proximal portion of the coupler such that rotation of the terminal pin relative to the lead body causes rotation and longitudinal translation of the coupler and the fixation helix relative to the flexible body; and a first electrode and a second electrode coupled to the flexible body in the distal region;

a multi-path conductor coil disposed longitudinally within the flexible body, the multi-path conductor coil including at least a first conduction path and at least a second conductive path electrically isolated from the first conductive path, the first conduction path electrically coupling the first electrode to the annular inner terminal ring and thereby the terminal pin through the one or more resilient C-clips, the second conduction path electrically coupling the second electrode to the outer terminal ring, the multi-path conductor coil being substantially fixed relative to the flexible body, and wherein the multi-path conductor coil has an impedance of several thousand ohms or greater when exposed to an external magnetic field characterized by 1.5 Tesla to 3.0 Tesla.

21. The electrical lead of claim 20, wherein the one or more resilient C-clips have a width between approximately $25/1000$ of an inch to approximately $50/1000$ of an inch and wherein the one or more resilient C-clips have an average diameter between approximately $20/1000$ of an inch to approximately $80/1000$ of an inch.

22. The electrical lead of claim 20, further including one or more layers of insulation between the terminal pin and the inner conductor ring housing.

\* \* \* \* \*